United States Patent [19]

LeVahn

[11] 4,355,631
[45] Oct. 26, 1982

[54] SURGICAL RETRACTOR APPARATUS WITH IMPROVED CLAMPING DEVICE

[75] Inventor: Bruce A. LeVahn, Robbinsdale, Minn.

[73] Assignee: Minnesota Scientific, Inc., Minneapolis, Minn.

[21] Appl. No.: 245,378

[22] Filed: Mar. 19, 1981

[51] Int. Cl.$^3$ .................. A61B 1/32; A61B 17/02
[52] U.S. Cl. .................. 128/20; 128/346; 128/17
[58] Field of Search ............ 128/20, 17, 87 R, 303 R, 128/346

[56] References Cited

U.S. PATENT DOCUMENTS

| | | | |
|---|---|---|---|
| 1,747,799 | 2/1930 | Straus | 128/20 |
| 2,586,488 | 2/1952 | Smith | 128/20 |
| 3,221,743 | 12/1965 | Thompson et al. | 128/303 |
| 3,572,326 | 3/1971 | Jensen | 128/20 |
| 3,823,709 | 7/1974 | McGuire | 128/20 |
| 3,910,538 | 10/1975 | Baitella | 248/121 |
| 4,254,763 | 3/1981 | McCready et al. | 128/20 |

FOREIGN PATENT DOCUMENTS

| | | | |
|---|---|---|---|
| 460145 | 5/1928 | Fed. Rep. of Germany | 128/20 |
| 1235135 | 5/1960 | France | 128/20 |
| 446439 | 3/1949 | Italy | 128/20 |

OTHER PUBLICATIONS

Poly-Tract Retractor System of Minnesota Scientific Inc., Thompson Retractor by Richard C. Thompson, M.D.
Codman & Shurtleff, Price List of Great Eastern Lumber Company, Inc.

*Primary Examiner*—Lee S. Cohen
*Assistant Examiner*—Angela D. Sykes
*Attorney, Agent, or Firm*—Kinney, Lange, Braddock, Westman & Fairbairn

[57] ABSTRACT

A retractor apparatus includes an improved clamping device on the sterile side of a surgical drape with the drape covering an operating table having side rails. The device includes a first member having a first clamping portion and a second member having a second clamping portion. The second member is pivotally attached to the first member. The first and second portions engage the sterile side of the surgical drape and when the second member is pivoted into a clamping position with the first member, the first and second portions clamp the surgical drape and side rail. A tightening mechanism retains the first and second clamping portions in the clamping position. The first and second members have first and second passages, respectively, that are substantially aligned with each other in both the clamping position and a nonclamping position. A support member of the surgical retractor apparatus extends through the first and second passages and is secured therein in a fixed position by a suitable mechanism.

7 Claims, 7 Drawing Figures

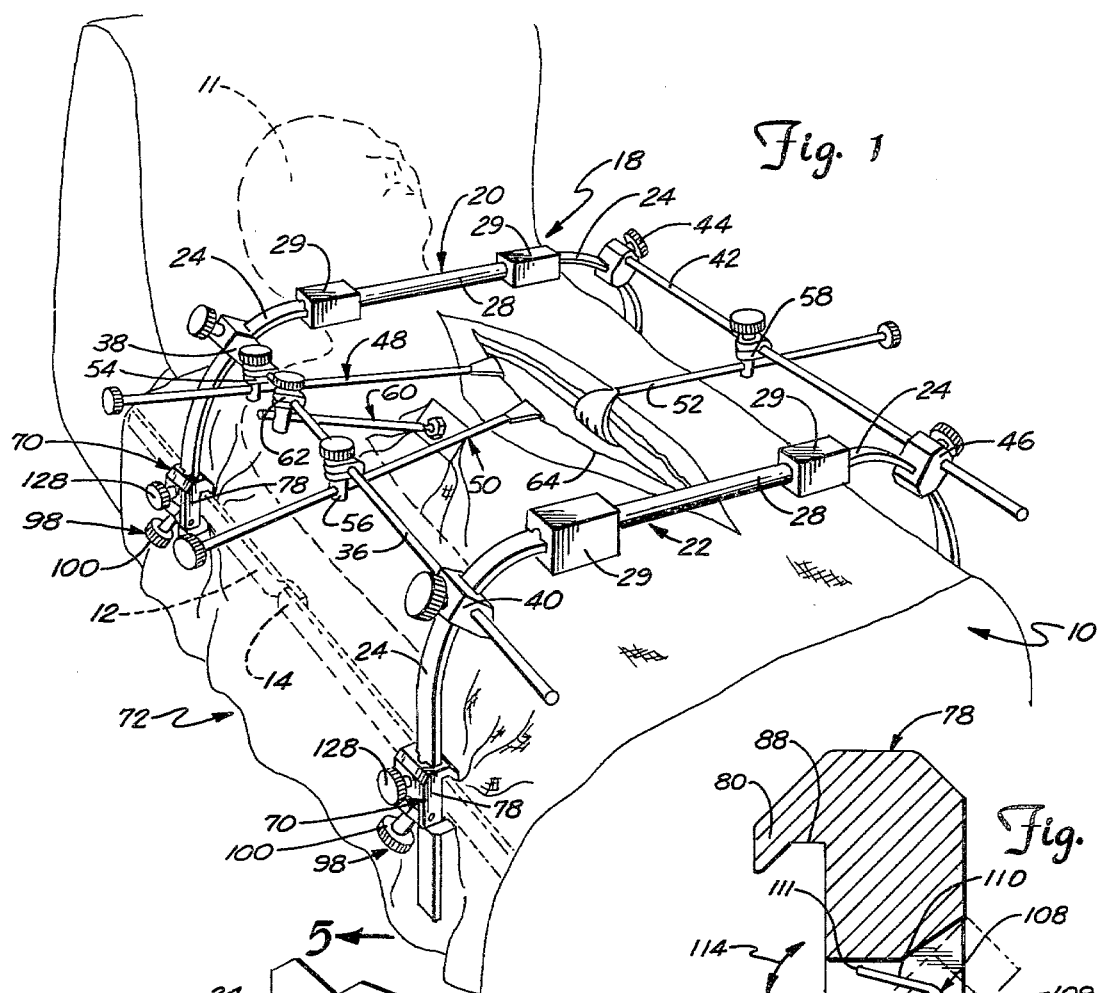
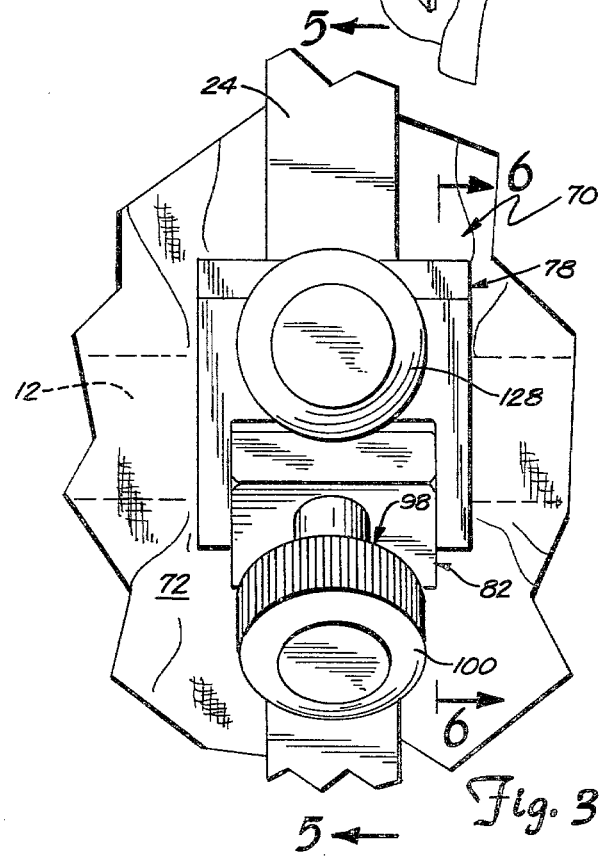
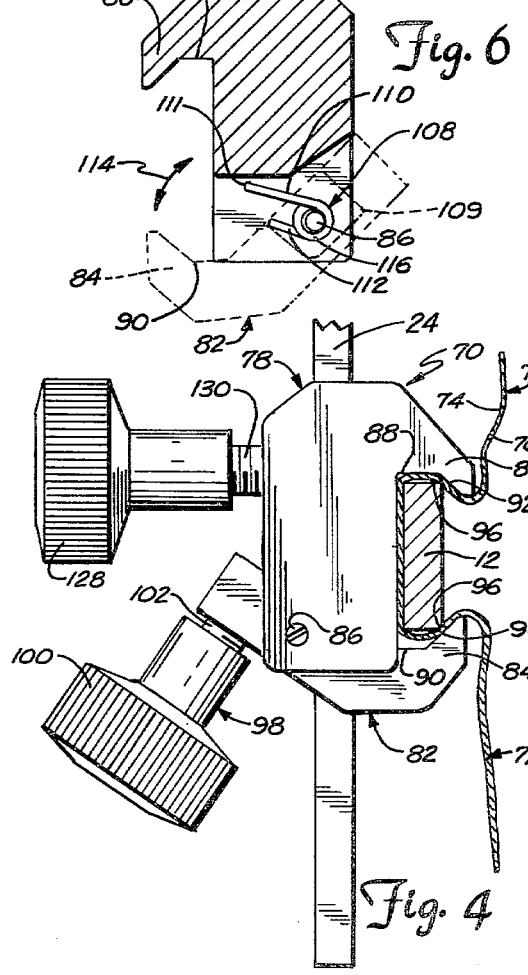

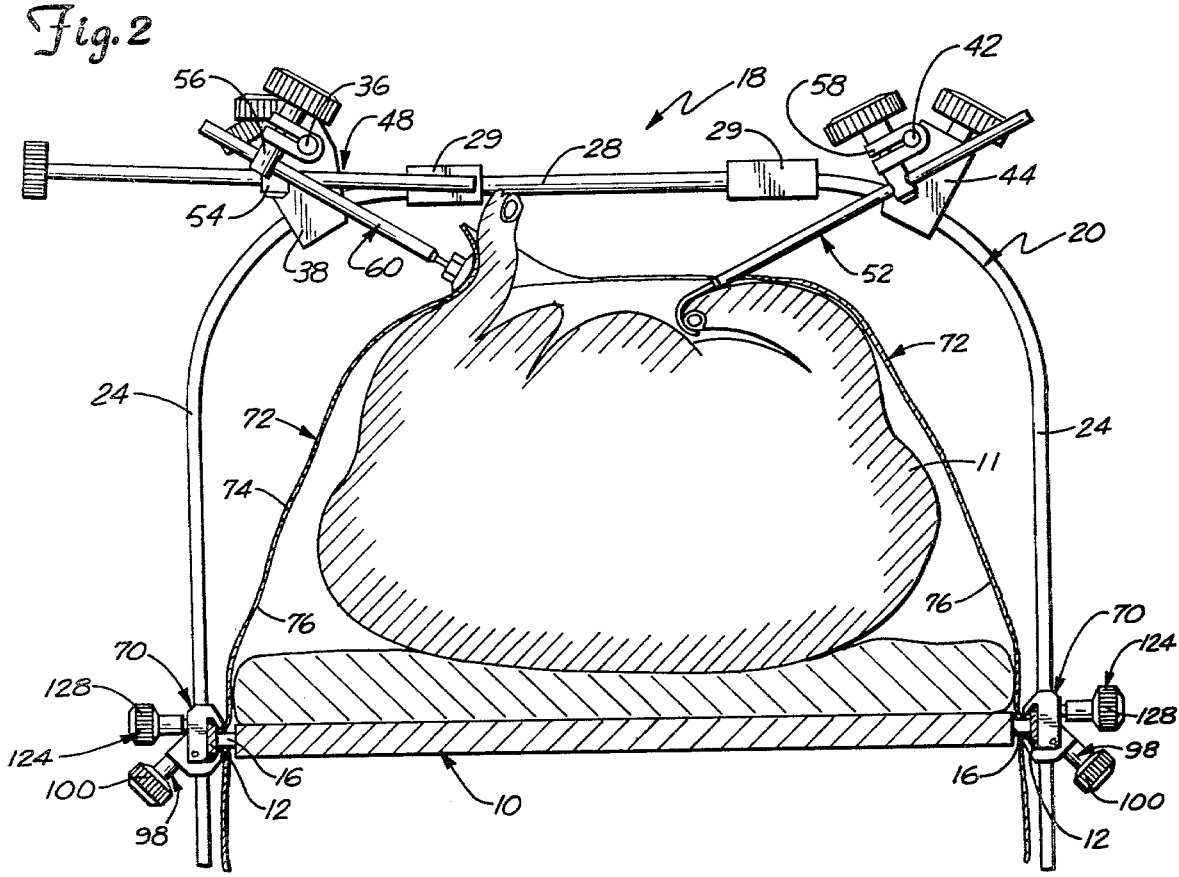
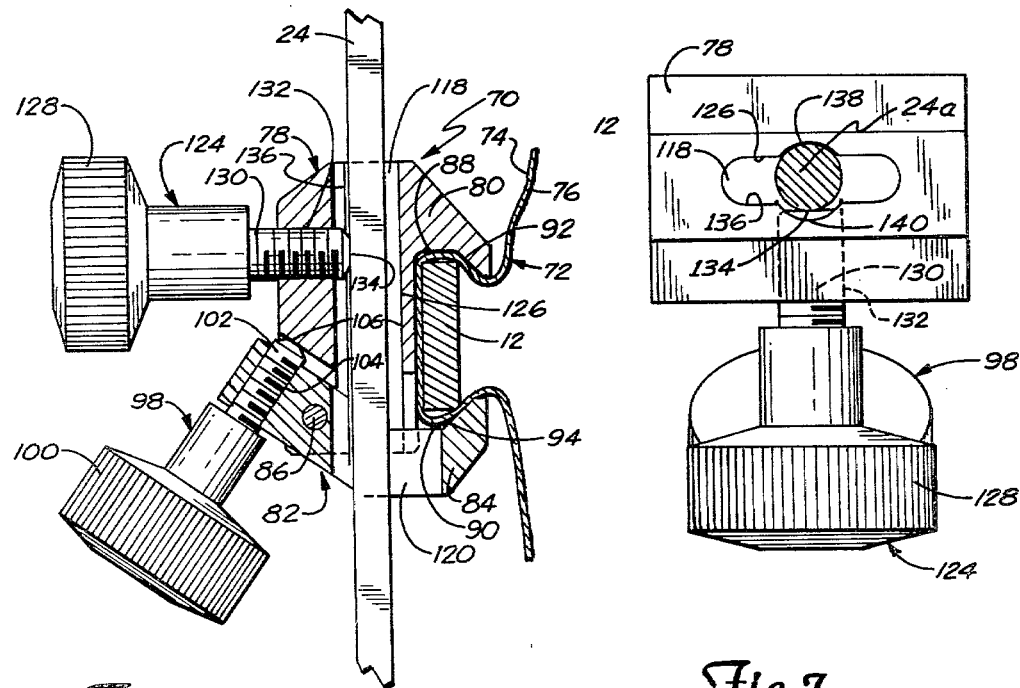
Fig. 2
Fig. 5
Fig. 7

SURGICAL RETRACTOR APPARATUS WITH IMPROVED CLAMPING DEVICE

BACKGROUND OF THE INVENTION

1. Field of the Invention

The present invention relates to surgical retractor apparatus, and in particular, it relates to clamping devices that support the retractor apparatus over an operating table.

2. Description of Prior Art

It is customary during major surgery, particularly on the chest or abdomen, to employ retractors. The retractors are applied to the edges of a surgical incision and pull back the incision exposing the area in which the surgeon must work. The retractor is held in place, typically, by being attached to a retractor apparatus that is positioned over the operating table. The retractor apparatus is usually attached to side rails located along the sides of the operating table by some type of clamping device.

In the prior art, many of the clamping devices on the side rails of the operating table had to be positioned in an exact location. The retractor apparatus was then secured to the clamping devices by various mechanisms to hold the retractor apparatus in place over the operating table. Since the side rails of the operating table are not sterile, a surgical drape was placed over the side rail by either cutting slits into the surgical drape and extending the supports of the retractor apparatus through the slits, or simply readjusting the drape around the support member and over the clamp and the side rail. The supports, being sterile, do not contaminate the sterile side of the surgical drape and the unsterile clamping device and side rail are on the other side of the surgical drape.

Some of the shortcomings of the above prior art clamping devices are that they do not allow the placement of the retractor apparatus to be varied easily in the horizontal direction along the length of the bed if slits are made in the drape. In addition, vertical adjustment of the retractor apparatus is difficult since the clamping device is beneath the drape. Introducing slits into the surgical drape, to allow the supports of the retractor apparatus to engage the clamping device presents a possible danger of contamination from the unsterile surfaces of the clamping device and the side rail through the slit.

Simply readjusting the surgical drape around the support member also presents a contamination problem. If the surgical drape is moved or shifts during the operation, the unsterile clamping device and part of the side rail may be exposed.

The following patents illustrate various clamping devices used to support surgical retractors on the side rails of operating tables:

Smith, U.S. Pat. No. 2,586,488—U.S.
Thompson, et al., U.S. Pat. No. 3,221,743—U.S.
Jensen, U.S. Pat. No. 3,572,326—U.S.
McGuire, U.S. Pat. No. 3,823,709—U.S.
Straus, U.S. Pat. No. 1,747,799—U.S.
D'Errico, Italian Pat. No. 446,439—Italian
Koltai, German Pat. No. 460,145—German
Pfister, French Pat. No. 1,235,135—French In addition, the assignee of the present application, Minnesota Scientific Inc., pictorially describes a prior art set-up procedure of a retractor system in a pamphlet entitled, "Poly-Tract Retractor System".

A retractor system made by Codman & Shurtleff, Inc. of Randolph, Massachusetts, includes a clamping device that clamps on to the side rail directly over the surgical drape. While the clamping device made by Codman & Shurtleff, Inc. avoids the contamination problem, the clamping device is complicated and not versatile. The clamping device has a screw-driven clamp at one end of a support post which clamps on to the side rail, and the lever to turn the screw of the clamp is positioned at the top end of the support post. In addition, the clamp is designed to hold no more than two double thicknesses of cotton surgical drapes against the siderail.

SUMMARY OF THE INVENTION

The present invention includes a retractor apparatus having an improved clamping device. The clamping device supports the retractor apparatus on the sterile side of a surgical drape over an operating table having side rails. The improved clamping device includes a first member with a first clamping portion and a second member pivotally attached to the first member having a second clamping portion. The first and second clamping portions engage the sterile side of the surgical drape against the side rail when the second member is pivoted into a clamping position. The first and second clamping portions are held in the clamping position by a tightening mechanism. The first and second members also include first and second passages, respectively, which extend fully therethrough and are aligned with each other. The first and second passages engage a support member of the retractor apparatus. A suitable mechanism holds the support member in a fixed position within the first and second passages, supporting the retractor apparatus above the operating table on the sterile side of the surgical drape.

BRIEF DESCRIPTION OF THE DRAWINGS

FIG. 1 is a perspective view of the retractor apparatus with the improved clamping device, the retractor apparatus being secured on the sterile side of the surgical drape to the side rail with the improved clamping device.

FIG. 2 is a cross-sectional view of the retractor apparatus in use, with a body being operated on, with the side rails and operating table, and longitudinal bars being shown in cross section.

FIG. 3 is a front view of the improved clamping device.

FIG. 4 is a side view of the improved clamping device with the surgical drape and side rail being shown in cross-section.

FIG. 5 is a cross-sectional view of the improved clamping device with parts shown whole for purposes of better clarity, taken along the line 5—5 in FIG. 3.

FIG. 6 is a cross-sectional view of the improved clamping device showing the bias spring with the lower member in phantom taken along the line 6—6 in FIG. 3.

FIG. 7 is a top view of the improved clamping device showing a cylindrical support member of the retractor apparatus in broken lines.

DETAILED DESCRIPTION OF THE PREFERRED EMBODIMENTS

Referring to FIG. 1, the retractor apparatus with an improved clamping device is shown in connection with an operating table 10 of conventional construction. Rigidly secured to each side of the operating table is a side rail 12 the side rail 12 may be hinged as indicated at 14 where the bed is of a design to permit tilting of one portion of the table 10 with respect to the other. The side rail 12 as shown in FIG. 2, is spaced outwardly from the bed, being secured thereto by posts 16. The frame 18, of the retractor apparatus, as shown in FIG. 1, preferably includes two inverted U-shaped support members 20 and 22. Each of the support members 20 and 22 actually consist of three separate members. Referring to the U-shaped member 20, the member includes two curved band members 24, and a removable center section 28. The U-shaped support 22, similarly, includes two curved band members 24 and a removable center section 28. The center sections 28 are connected to the curved band members by connector members 29.

Adjustably secured to the curved members 24 are longitudinal rods 36 and 42, preferably of circular cross-section. The rod 36 extends through apertures in clamps 38 and 40. Similarly, the longitudinal rod 42 extends through apertures in clamps 44 and 46. Clamps 38, 40, 44 and 46 are movable along the curved members 24.

Various implements are adjustably secured to the rods 36 and 42. As shown in FIG. 1 and 2 for purposes of illustration, retractors 48, 50 and 52 are secured to the rods 36 and 42 by clamps 54, 56 and 58 respectively. A pusher 60 is also adjustably attached to bar 36 by clamp 62. The retractors and pusher in combination, hold the portions of the body 11 along the edges of a surgical incision in a manner as to expose the area on which a surgeon must work. It should be understood, that the present invention is not limited to the above described retractor apparatus and includes other retractor apparatuses which are secured by support members to the side rails 12 of the operating table 10.

An improved clamping device, generally indicated at 70 secures a surgical drape 72 by clamping the surgical drape 72 against the side rail 12. The surgical drape 72 is a conventional surgical drape having been sterilized and when placed on an operating table has a side 74 which is maintained sterilized and a side 76 which is not maintained sterilized, thus side 74 may be referred to as the sterilized side and side 76 as the unsterilized side. The surgical drape 72 is placed over the body 11, which is unsterilized, to prevent infection in the area of the incision 64. The improved clamping device 70, in addition, supports the retractor apparatus 18 by engaging the support members 24, and retains the support members in a fixed position with respect to the operating table 12.

The improved clamping device 70 is illustrated in more detail in FIGS. 3-6. The clamping device 70 includes an upper member 78 with an upper clamping portion 80 for engagement with the side rail 12 over the surgical drape 72. A lower member 82 with a lower clamping portion 84 is pivotally attached to the upper member 78 preferably by a pivot pin 86. The clamping portion 84 of the lower member 82, similarly, engages the side rail 12 through surgical drape 72. The clamping portions 80 and 84 preferably have substantially planer upper and lower surfaces 88 and 90, respectively. Beveled edges 92 and 94 define a gripping edge that grips the back corners 96 of the side rail 12. The lower member 82 pivots to a clamping position about pivot pin 86 with first and second clamping portions gripping the corners 96 and holding the surgical drape 72 in place. The upper and lower clamping portions 80 and 84, although shown gripping one thickness of surgical drape against a side rail having a rectangular cross-section, can grip a plurality of surgical drapes against various cross-sectional configurations of side rails.

Preferably, the clamping device is held in the clamping position around the side rail 12 by tightening mechanism 98. The tightening mechanism 98 has a clamping knob 100 fixedly attached to a cylindrical threaded shaft 102 at one end which threadably engages a threaded passage 104, as shown in FIG. 5. The shaft 102 has another end 106 which engages a lower outer surface of the upper member 78. The clamping device is placed in the clamping position by screwing the shaft 102 through the threaded passage 104. The end 106 of the shaft 102 engages the lower outer surface of the upper member 78 when the shaft 102 is threaded through passage 104. The shaft 102 when screwed through the passage 104 provides a force to pivot the lower member 82 about the pivot pin 86 with the lower clamping portion 84 moving toward the upper clamping portion 80. The clamping device is in the clamping position when the tightening mechanism 98 cannot be turned further by using reasonable force. To disengage the upper and lower clamping portions from the clamping position, the clamping knob 100 is turned in an opposite direction withdrawing the end 106 from the lower surface of the upper member 78.

Referring to FIG. 6, a spring 108 provides a biasing force to the upper member 78 and the lower member 82 biasing the clamping portions 80, 84 apart. Thus, when tightening mechanism 98 is turned to release the clamping device 70 from the clamping position, the spring 108 cooperates with the tightening mechanism 98 in moving the clamping portions 80 and 84 away from side rail 12 and surgical drape 72. The spring 108 preferably sits in a depression 109 that is machined in the lower member 82. The spring 108 has an upper member 110 preferably bent at a right angle and secured within an aperture 111, and a lower member contacting portion 112 which biases the upper member 78 and the lower member 82 in the direction indicated by arrow 114. A loop 116 of the spring 108 surrounds the pivot pin 86 to hold the spring 108 in place. It should be understood that any type of biasing component is within the scope of the present invention.

An upper passage 118 preferably extends through the upper member 78 in a substantially vertical direction perpendicular to the longitudinal axis of the side rail 12. Similarly, a lower passage 120 extends through lower member 82 in a perpendicular direction with respect to the longitudinal axis of the side rail 12. The upper passage 118 and the lower passage 120 are aligned with each other and accept a straight portion of the curved support member 24. The lower passage 120 is larger than the upper passage 118 in a direction of the pivotal movement of the lower member 82. The larger diameter of the lower passage 120 allows the lower member 82 to pivot into the clamping position and from the clamping position without interference of the curved support member 24. In effect, the diameter of the lower passage 120 is sufficiently large that the upper passage 118 is aligned with at least some portion of the lower passage 120 sufficiently large to accept the curved support member 24.

The upper passage 118 has a first side 126 and second side 136 parallel to the side 126. The passage 118 having parallel sides accepts support members 24 of a substantially rectangular cross-section, as shown in FIG. 5. In addition, the passage 118 preferably has semi-cylindrical portions 138 and 140 approximately in the center of and running along the entire length of the sides 126, 136, respectively. As shown in FIG. 7. The semi-cylindrical portions 138 and 140 in combination with the passage 118 accept a cylindrical support member 24a.

To retain the curved support member 24 in a fixed position within the passage 118 and 120 and support the retractor assembly 18, preferably a tightening mechanism 124 forces curved support member 24 against surface 126 of the upper passage 118, as best seen in FIGS. 5. The tightening mechanism 124 forcing cylindrical support member 24a against semi-cylindrical portion 138 is best seen in FIG. 7. The tightening mechanism 124 has a set screw 130 with a knob 128 of sufficient size to fit comfortably in a hand so that the set screw 130 can be turned with considerable force. The set screw 130 threadably engages a threaded passage 132 in the upper chamber 78 and has a free end 134 projecting out of the passage 132 that engages the support member 24. The set screw 130 frictionally holds the support member 24 against the surface 126 and retains the support member 24 in a fixed and secure position. The set screw 130 is positioned in the upper member 78 to engage either the rectangular support member 24 or the cylindrical support member 24a.

In use the surgical drape is placed over the patient with a lower end of the drape lying on the operating table. The surgical drape, being sterilized, provides a sterile environment of the forthcoming operation on the patient. The clamping device, also being sterile, is clamped at the appropriate position over the lower end of the surgical drape onto the side rail. The clamping device is clamped onto the side rail by turning the clamping knob 100 and forcing the end 106 of the shaft 102 against the surface of the upper member 78. The lower member 82 will pivot to the clamping position. The support member is then placed into the passages 118 and 120, and secured in the appropriate vertical position by turning the tightening mechanism 124 to force the upper member against side 126 of the upper passage. A clamping device for each support member is similarly attached to the side rails of the operating table. The rest of the retractor apparatus, as shown in FIG. 1, is then attached initially to the support members and the other elements of the retractor apparatus to complete the assembly of the apparatus.

The entire retractor apparatus is easily adjusted along the horizontal length of the operating table by simply turning clamping knob 100 to unclamp the clamping device and move the device along the side rail. To adjust the retractor apparatus in the vertical direction, knob 128 is turned in a direction that releases the support member. The support member is then adjusted and clamping knob 128 is turned in the other direction to retain the retractor apparatus in a fixed position. Since the clamping device is on the sterile side of the surgical drape, both vertical and horizontal adjustments are easily made without endangering the sterile environment from contamination from underneath the surgical drape. In addition, the clamping device of the present invention holds the surgical drape in place over the operating table.

Although the present invention has been described with reference to the preferred embodiments, persons skilled in the art will recognize that changes may be made in form and detail without departing from the spirit and scope of the invention.

What is claimed is:

1. A retractor apparatus for fastening to the side rails of an operating table covered by a surgical drape having a sterile and an unsterile side, said retractor apparatus including support members to be secured to the side rails and extending upwardly above the level of said operating table surgical retractors adjustably secured to said support members and, clamping devices for securing said support members to said side rails and supporting said apparatus on the sterile side of said surgical drape covering the operating table, each of said clamping devices comprising:

a first member having a first clamping portion for engaging the sterile side of the surgical drape to clamp the unsterile side of the surgical drape against the side rail and having a first passage extending therethrough, through which one of the support members extends;

a second member pivotally attached to the first member having a second clamping portion for engaging the sterile side of the surgical drape to clamp the unsterile side of the surgical drape against the side rail, the second member pivoting to a clamping position with the first clamping member, and said second member having a second passage extending therethrough alignable with the first passage, the support member of the retractor apparatus extending from the first passage into and through the second passage;

means for tightening the first and second clamping members into the clamping position; and means for holding the support member of the retractor apparatus in fixed position within the first and second passages.

2. The apparatus of claim 1 wherein the means for tightening the first and second clamping portions into the clamping position is a first clamping knob from which a threaded shaft extends, said shaft threadably engaging and extending through a threaded hole in the second member and engaging the first member with a free end on a side of the pivotal attachment opposite from the second clamping portion such that when the clamping knob is turned inwardly to turn the threaded shaft with respect to the threaded hole, the second member is pivoted about a pivot point pivoting the second clamping portion toward the first clamping portion.

3. The apparatus of claim 1 wherein the means for holding the support member of the retractor apparatus is a second clamping knob from which a threaded shaft extends, said shaft engaging and extending through a threaded passage, the threaded passage extending from the outside of the first member into the first passage wherein a free end of the threaded shaft engages the support member of the retractor apparatus, holding the support member against a side of the passage thereby frictionally retaining the support member in a fixed position.

4. The apparatus of claim 1 and further including a spring bias means biasing the second clamping portion away from the first clamping portion.

5. The apparatus of claim 1 wherein the first passage has two substantially parallel opposite facing sides for receiving a support member having a substantially rectangular cross section.

6. The apparatus of claim 1 or 5 wherein the first passage has surfaces extending through its length that substantially conform to and receive a cylindrical support member of the retractor apparatus.

7. The apparatus of claim 1 wherein the second passage is larger than the first passage in a direction of the pivotal movement of the second member and is sufficiently large that the second member pivots without interference from the support member of the retractor apparatus.

* * * * *